United States Patent
Nolan

[11] Patent Number: 6,117,174
[45] Date of Patent: Sep. 12, 2000

[54] SPINAL IMPLANT DEVICE

[76] Inventor: Wesley A. Nolan, 7766 Chatfield La., Elliott City, Md. 21043

[21] Appl. No.: 09/154,327

[22] Filed: Sep. 16, 1998

[51] Int. Cl.⁷ ............... A61F 2/44; A61F 2/30; A61B 17/00
[52] U.S. Cl. .................. 623/17.11; 623/18.11; 623/17.16; 623/908; 606/61
[58] Field of Search ............... 623/17, 16, 66, 623/17.11, 17.16, 18.11, 908; 606/61, 60, 63, 73

[56] References Cited

U.S. PATENT DOCUMENTS

| | | | |
|---|---|---|---|
| 4,501,269 | 2/1985 | Bagby | 128/92 G |
| 4,743,256 | 5/1988 | Brantigan | 623/17 |
| 4,820,305 | 4/1989 | Harms et al. | 623/16 |
| 4,834,757 | 5/1989 | Brantigan | 623/17 |
| 4,878,915 | 11/1989 | Brantigan | 623/17 |
| 4,904,261 | 2/1990 | Dove et al. | 623/17 |
| 4,961,740 | 10/1990 | Ray et al. | 606/61 |
| 5,015,247 | 5/1991 | Michelson | 606/61 |
| 5,026,373 | 6/1991 | Ray et al. | 606/61 |
| 5,055,104 | 10/1991 | Ray | 606/61 |
| 5,059,193 | 10/1991 | Kuslich | 606/61 |
| 5,263,953 | 11/1993 | Bagby | 606/61 |
| 5,306,309 | 4/1994 | Wagner et al. | 623/17 |
| 5,397,364 | 3/1995 | Kozak et al. | 623/17 |
| 5,403,136 | 4/1995 | Mathys | 411/310 |
| 5,423,817 | 6/1995 | Lin | 606/61 |
| 5,425,772 | 6/1995 | Brantigan | 623/17 |
| 5,443,514 | 8/1995 | Steffee | 623/17 |
| 5,489,307 | 2/1996 | Kuslich et al. | 623/17 |
| 5,489,308 | 2/1996 | Kuslich et al. | 623/17 |
| 5,522,899 | 6/1996 | Michelson | 623/17 |
| 5,534,031 | 7/1996 | Matsuzaki et al. | 623/17 |
| 5,554,191 | 9/1996 | Lahille et al. | 623/17 |
| 5,593,409 | 1/1997 | Michelson | 606/61 |
| 5,609,635 | 3/1997 | Michelson | 623/17 |
| 5,609,636 | 3/1997 | Kohrs et al. | 623/17 |
| 5,645,598 | 7/1997 | Bronsahan, III | 623/17 |
| 5,653,763 | 8/1997 | Errico et al. | 623/17 |
| 5,658,337 | 8/1997 | Kohrs et al. | 623/17 |
| 5,665,122 | 9/1997 | Kambin | 623/17 |
| 5,669,909 | 9/1997 | Zdeblick et al. | 606/61 |
| 5,683,463 | 11/1997 | Godefroy et al. | 623/17 |
| 5,709,683 | 1/1998 | Bagby | 606/61 |
| 5,716,415 | 2/1998 | Steffee | 623/17 |

Primary Examiner—David H. Willse
Assistant Examiner—Choon P. Koh
Attorney, Agent, or Firm—Webb Ziesenheim Logsdon Orkin & Hanson, P.C.

[57] ABSTRACT

A dynamic fusion device for facilitating arthrodesis in a disc space between adjacent vertebrae that includes a body and an engaging member. The body extends along a longitudinal axis having a first portion and two or more legs depending from the first portion. The legs are laterally spaced apart from each other and define a second end of the body spaced opposite the first end. The legs define an engaging member receiving cavity. An engaging member, such as a disc, is secured to the body and received within the engaging member receiving cavity, wherein the engaging member is secured to the body only by engagement of the engaging member with the legs. During installation, the engaging member causes the legs to flex.

29 Claims, 5 Drawing Sheets

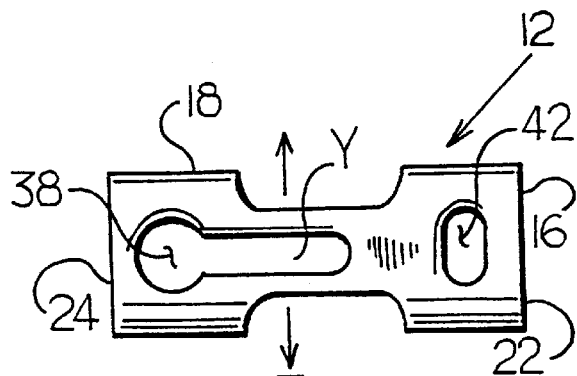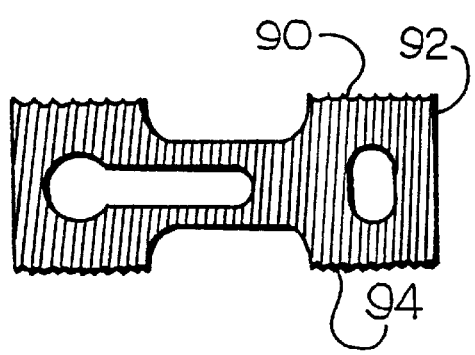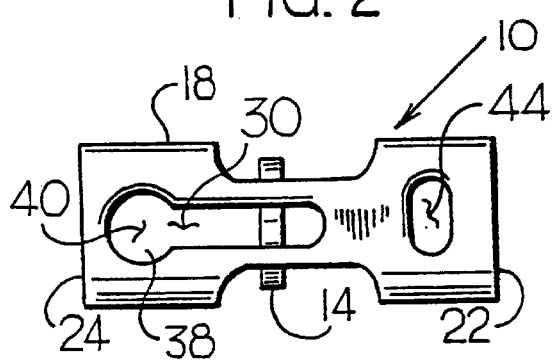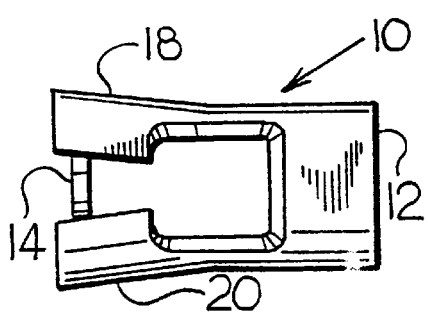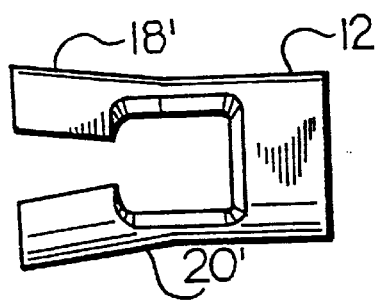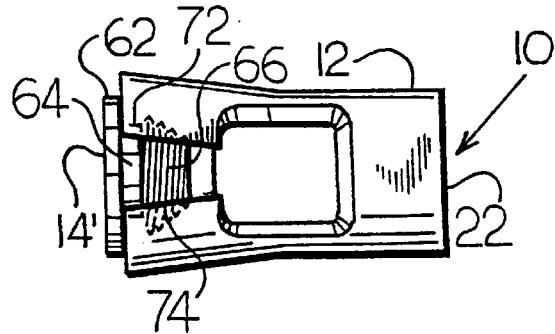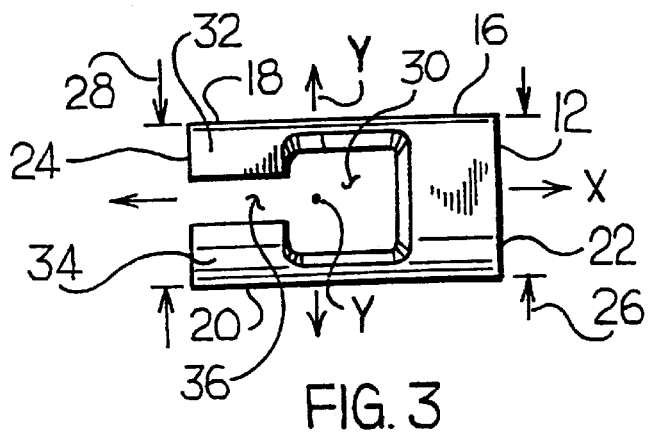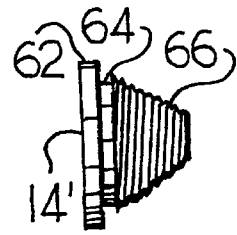

SPINAL IMPLANT DEVICE

BACKGROUND OF THE INVENTION

1) Field of the Invention

The present invention relates to surgical procedures for stabilizing the spine, restoring disc height and reestablishing anatomic curves of the spine and, more particularly, to a spinal implant device for use in such procedures.

2) Description of the Prior Art

The human spinal column includes over twenty bones or vertebrae. Spinal disc cartilage is positioned between the adjacent vertebrae. Through the wear and tear of everyday living, damage can occur between the spinal disc cartilages positioned between the adjacent vertebrae or the vertebra itself. This degeneration can cause excessive back pain.

A number of procedures and devices has been developed to correct this problem, such as interbody fusion devices. One of the most popular interbody fusion devices has taken on the form of a cylindrical implant, such as described in U.S. Pat. Nos. 4,501,269; 4,743,256; 4,834,757; 4,878,915; 4,961,740; 5,015,247; 5,055,104; and 5,192,327. These cylindrical implants can either be threaded or pounded into the disc space between the adjacent vertebrae.

In each of the above-identified patents, the cross section of the implant is constant throughout its length and is typically in the form of a right circular cylinder. An advantage of the circular design is that current surgical drills can easily drill a substantially circular profile into a bone. The bone is more difficult to prepare for other profiles.

However, one problem encountered with these prior art devices is that they do not maintain or restore the normal anatomy of the fused spine segment. In other words, once the disc is removed, the normal lordotic or kyphotic curvature of the spine is eliminated.

Several attempts have been made to provide implants that attempt to restore the curvature of the spine. U.S. Pat. Nos. 5,669,909 and 5,683,463 provide one-piece, frusto-conical shaped implants. Although in theory these implants may restore the curvature of the spine, they are difficult to install since special reamers may be needed to provide a tapered hole or a cylindrical hole must be modified by the implant which could put undue stress on the adjacent vertebrae.

U.S. Pat. No. 5,653,763 describes a multi-piece rectangular-shaped dynamic implant that includes rectangular-shaped legs hinged at one end. An arrangement for separating the legs is provided that includes a shaft and a nut received within an interior space defined by the legs. This device requires special surgical tools to prepare a rectangular space between the adjacent vertebrae. Further, the hinged body may affect the integrity of the implant over time. Also, this device has no areas to receive bone mass to facilitate healing.

U.S. Pat. No. 5,554,191 discloses an intersomatic vertebrae cage inserted from the posterior approach between two vertebra. This arrangement includes an integral body having two legs with a multi-piece adjustment mechanism to adjust the spacing between the legs. The cage is rectangular in cross section and has no areas defined to receive bone mass to facilitate healing.

Therefore, it is an object of the present invention to provide a spinal implant device that is relatively easy to install either posteriorly or anteriorly, maintains the appropriate curvature of the spine and facilitates healing.

SUMMARY OF THE INVENTION

The present invention is a dynamic fusion device for facilitating arthrodesis in a disc space between adjacent vertebrae that includes a body and an engaging member secured to the body. The body can be made from either titanium, nitinol, stainless steel or other bio-compatible material. The body extends along a longitudinal axis having a first portion and two or more legs depending from the first portion. The first portion has a first end with a width of a first lateral distance. Preferably, the first portion is substantially cylindrical in shape and the first portion can be hollow. The legs are laterally spaced apart from each other and define a second end of the body spaced opposite from the first end. The second end has a width of a second lateral distance. The legs define an engaging member receiving cavity. Preferably, the legs are spaced apart from each other and define a passageway through the body. The passageway extends along an axis transverse to the longitudinal axis. Preferably, the first portion and the legs have curved outer surfaces, each of the outer surfaces having the same radius of curvature. The engaging member is secured to the body and received within the engaging member receiving cavity, wherein the engaging member is secured to the body only by engagement of the engaging member with the legs. Preferably, the engaging member includes a threaded passageway for threadably receiving an adjustment rod for engaging the engaging member with the legs. Preferably, the engaging member is a disc.

The engaging member slidably contacts the body whereby when the engaging member is positioned at a first position, the second lateral distance can equal the first lateral distance, or be less than or greater than the first lateral distance, and when the engaging member is positioned at a second position, the engaging member causes the legs to flex and the second lateral distance is different from the first lateral distance. Preferably, at least one of the legs includes an inner surface that defines a ramp whereby movement of the engaging member along the longitudinal axis contacts the ramp causing the leg to flex in a lateral direction and varying the second lateral distance. Preferably, when the second engaging member is positioned at the second position, the second lateral distance is greater than the first lateral distance. Also, when the engaging member is positioned at the second position, the engaging member is adjacent the second end.

The body can have an outer surface with a radial projection or more preferably, a plurality of radial projections extending therefrom such as in the form of threads. The threads can be positioned on either the first portion or the legs or both.

The first portion can also include an inner surface that defines a hollow cavity which is in communication with the engaging member receiving cavity. The hollow cavity can be open ended. An end cap can be provided to close off the open end of the passageway. The end cap can be made of polymeric material. Preferably, the first portion defines one or more passageways for permitting bone mass to grow therethrough.

The present invention is also a method for installing the above-described dynamic fusion device for facilitating arthrodesis in a disc space between adjacent vertebrae that includes the steps of: forming a body receiving passageway between two adjacent vertebrae for receipt of a substantially cylindrical-shaped insert; inserting the body into the body receiving passageway; and securing the engaging member to the second end of the body causing the legs to flex so that the second lateral distance increases whereby the second lateral distance is greater than the first lateral distance and the engaging member is only held in place by the legs. The method can further include the steps of: placing bone tissue within the engaging member receiving cavity and a bone receiving cavity defined in the first portion of the body; securing an end cap to the first end of the body after the bone tissue has been placed within the first portion; and/or installing a second dynamic fusion device between the adjacent vertebrae which is adjacent to the installed fusion device.

BRIEF DESCRIPTION OF THE DRAWINGS

FIG. 2 is a plan view of a body of a spinal implant device made in accordance with the present invention;

FIG. 3 is a side elevational view of the body shown in FIG. 2;

FIG. 7 is a plan view of the body shown in FIG. 2 having a disc received therein made in accordance with the present invention;

FIG. 8 shows a side elevational view of the body and disc shown in FIG. 7 with the disc in a second position;

FIG. 11 is a side elevational view of the body, wherein legs of the body diverge;

FIG. 12 is a side elevational view of the body shown in FIG. 2 with a disc received therein;

FIG. 13 is an elevational view of the disc shown in FIG. 12;

FIG. 14b is a side elevational view of the plug shown in FIG. 14a;

FIG. 14c is an end elevational view of the plug shown in FIG. 14a;

FIG. 18 is another embodiment of a spinal implant device similar to the body shown in FIG. 2 having a threaded outer surface;

DESCRIPTION OF THE PREFERRED EMBODIMENTS

Figure 1:
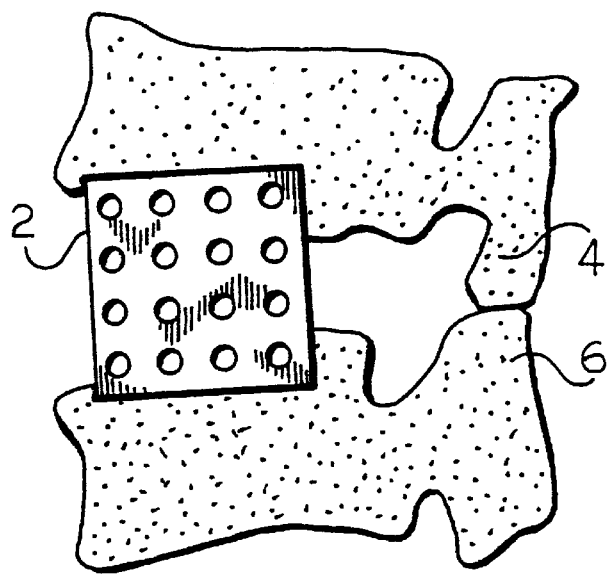
FIG. 1 shows a side elevational view of a fusion device of the prior art.

FIG. 1 shows a prior art unitary spinal implant device 2 having a right cylindrical shape secured in a disc space between two adjacent vertebrae 4 and 6. This type of device affects the natural curvature of the spine.

FIGS. 2–13 show a spinal implant device or dynamic fusion device 10 for facilitating arthrodesis in a disc space between adjacent vertebrae made in accordance with the present invention, which when implanted, restores the natural curvature of the spine. The spinal implant device 10 includes a body 12 and an engaging member or disc 14.

Figure 4:
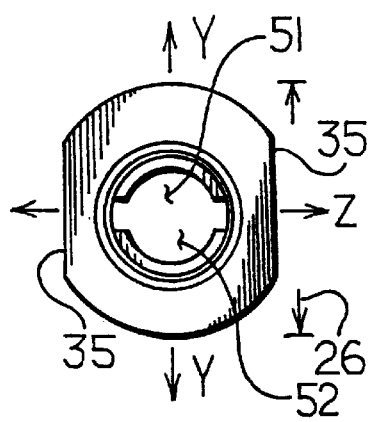
FIG. 4 is a forward end view of the body shown in FIG. 2.
Figure 5:
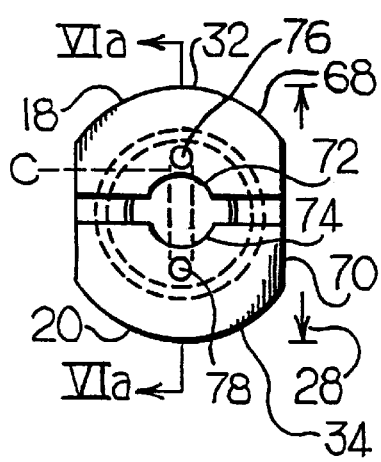
FIG. 5 is a rearward end view of the body shown in FIG. 2.

Referring specifically to FIGS. 2 and 3, the body 12 extends along a longitudinal axis X and includes a first portion 16 having two legs 18 and 20 extending therefrom. The body 12 includes a first end or forward end 22 and a second end or rearward end 24 positioned opposite the first end 22. The first end 22 has a width 26 which is a first lateral distance as shown in FIG. 4. The second end 24 has a width 28 which is a second lateral distance as shown in FIG. 5. The widths 26 and 28 can be equal to each other or width 28 can be greater than or less than width 26. Referring back to FIG. 3, the legs 18 and 20 define an engaging member receiving cavity or disc receiving cavity 30. Preferably, the body 12 is made of stainless steel, titanium, nitinol or any other biocompatible material which will provide rigidity, but permit the legs 18 and 20 to flex.

Figure 6B:
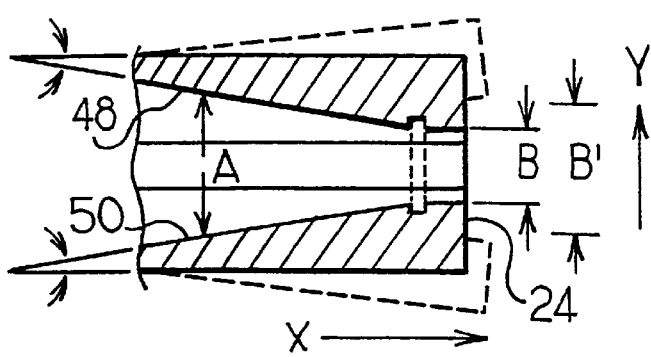
FIG. 6b is a partial, sectional view of a portion of a body of a spinal implant device shown in FIG. 2.
Figure 6A:
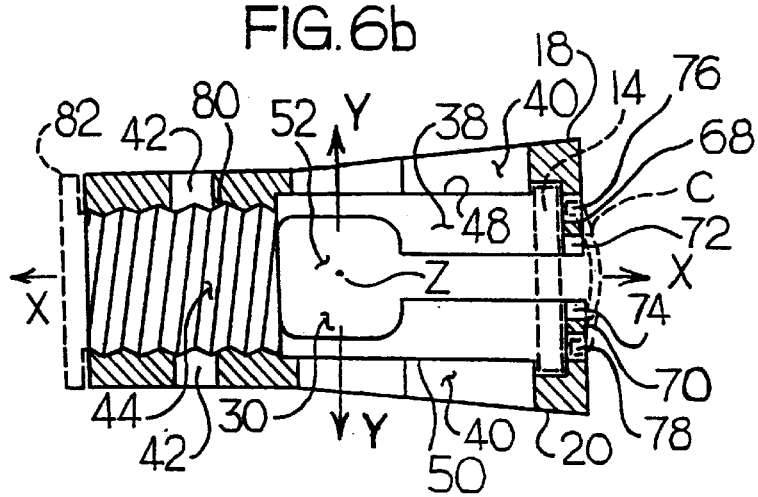
FIG. 6a is a sectional view taken along lines VIa—VIa of FIG. 5.

As shown in FIG. 5, the legs 18 and 20 have curved outer surfaces 32 and 34, which have a radius of curvature that is less than, greater than or equal to the radius of the first portion 16 as shown in FIG. 4. The first portion 16 is substantially cylindrical in shape having flats 35 defined on opposite sides. Alternatively, the first portion 16 can be cylindrically shaped. As shown in FIGS. 2, 3, 6a and 7, the legs 18 and 20 also define several passageways 36 and 38 that extend along axes Y and Z which are transverse to the longitudinal axis X. As shown in FIGS. 6a and 7, passageway 38 is defined by holes 40 defined in legs 18 and 20. Also, a plurality of holes 42 is defined in the first portion 16 defining a passageway 44. A through-hole 51 is defined by an inner surface 48 of the first portion 16, which is in communication with the disc receiving cavity 30 and defines a bone receiving cavity 52. The passageways 36, 38 and 44 facilitate bone growth through the body both along axes Y and Z.

Referring to FIGS. 5 and 6a, the legs 18 and 20 include two lips 68 and 70 that face each other. Each of the lips 68 and 70 includes arcuate inner surfaces 72 and 74, respectively, which define a portion of the disc receiving cavity 30. Each of the lips 68 and 70 includes holes 76 and 78 which are laterally spaced apart. Also, as shown in FIG. 6a, the first portion 16 defines a threaded inner surface 80 that defines an open ended passageway, which is adapted to receive an end plug 82, shown in phantom, to close off the open ended passageway.

Figure 9:
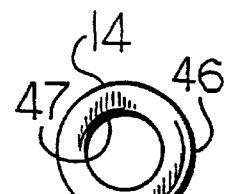
FIG. 9 shows a plan view of the disc shown in FIG. 7.
Figure 10:
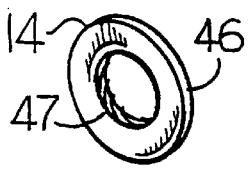
FIG. 10 is a perspective view of the disc shown in FIG. 9.

With reference to FIGS. 9 and 10, the disc 14 is ring shaped and has an outer surface 46 and a threaded inner surface 47. The inner surface 47 may or may not be threaded. Preferably, the disc 14 is made of the same material as the body 12, although they can be made of different materials. FIG. 7 shows the disc 14 received within the disc receiving cavity 30 and positioned between the first end 22 and the second end 24. Preferably, as shown in FIGS. 6a and 6b, inner surfaces 48 and 50 of the legs 18 and 20 are curved and/or inclined and have the same shape whereby a lateral distance A defined between the inner surfaces of the legs varies along the longitudinal axis X (see FIG. 6b). Preferably, the lateral distance A decreases along the longitudinal axis X moving toward the second end 24 and into recessed slots defined near the second end 24 prior to positioning the disc 14 within the disc receiving cavity 30. Hence, the disc 14 is moved toward the second end 24, the outer surface 46 of the disc 14 contacts the inner surfaces 48 and 50 of the legs 18 and 20, which are then flexed and forced apart in a lateral direction along the Y axis thereby moving the inner surfaces 48 and 50 at the second end 24 apart from a distance B to B' as shown in FIGS. 6b and 8.

FIG. 11 shows the body 12 having legs 18' and 20' diverging in an outwardly direction as opposed to extending in a straight direction shown in FIG. 3. The body 12 can be formed in the arrangement shown in FIG. 11. A removable clip C, shown in phantom in FIGS. 5 and 6a, can be provided and received in holes 76 and 78 to cause the legs 18' and 20' to look like legs 18 and 20. The clip C can then be removed during installation with the aid of calipers or tweezers. The clip C is shown installed externally of the body 12. Clip C can also be positioned within the interior of the body 12.

FIGS. 12 and 13 show an alternate disc 14'. Disc 14' includes two circular portions 62 and 64 and a tapered threaded portion 66. As shown in FIG. 12, the threaded portion 66 initially engages with arcuate inner surfaces 72 and 74. Rotation of disc 14' in a clockwise direction about the longitudinal axis X causes the disc 14' to move toward the first end 22 until the circular portion 64 contacts the inner surfaces 72 and 74 at which point the inner surfaces 72 and 74 are sandwiched between the circular portion 62 and the threaded portion 66.

Installation of the spinal implant device 10 is described below. In a posterior installation, initially the spinal disc area between two adjacent vertebrae is identified. The diseased spinal disc is removed.

Figure 14A:
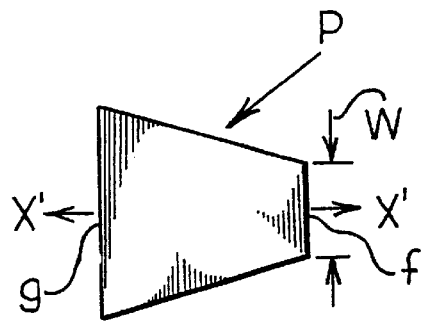
FIG. 14a is a top plan view of a plug used to install the spinal implant device made in accordance with the present invention.
Figure 14B:
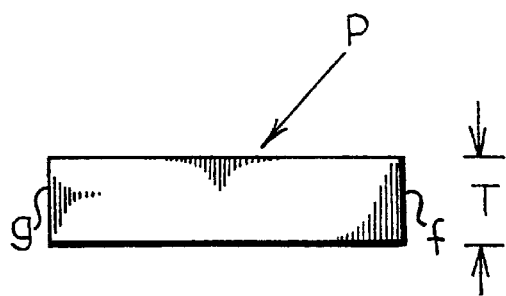
Figure 14C:
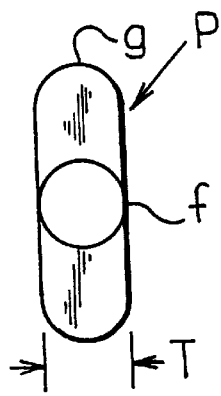

As shown in FIGS. 14a–14c, two plastic plugs P are then to be inserted into the disc space defined between the adjacent vertebrae. Plugs P are tapered having a first end f having a circular shape and a second end g having semi-circular shaped ends and straight sides, wherein the length of g is greater than the length of f. The thickness of the plug is T and the plug has a varying width W. The thickness of the plug T is equal to the diameter of the circle defined at the first end f.

Figure 14D:
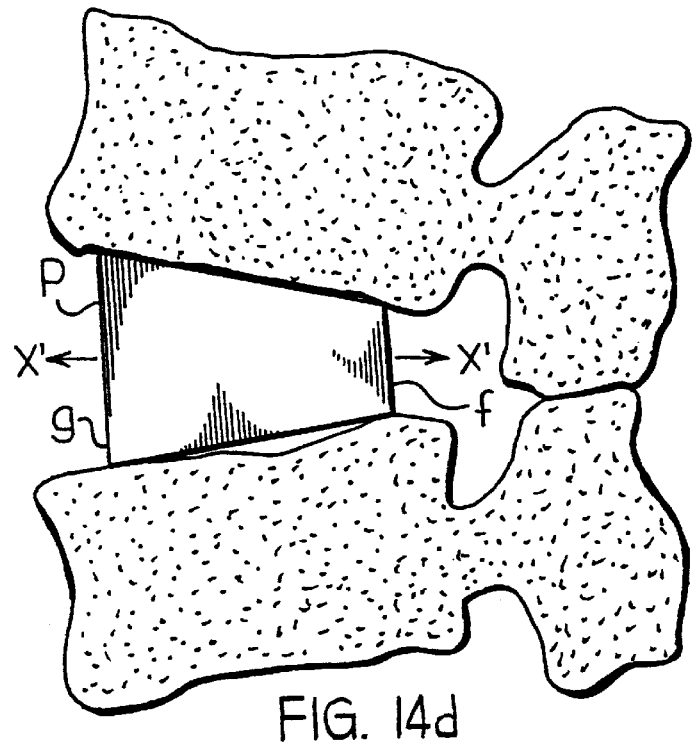
FIG. 14d is an elevational view of the plug shown in FIG. 14a installed between two adjacent vertebrae.

A surgeon installing the spinal implant device 10 must determine the appropriately sized plug, namely, the minimum and maximum width W and the thickness T of the plug P. Initially, a first plug P is inserted flat into the disc space on its side, as shown in FIG. 14b, so that second end g faces anteriorly in the patient and the plug P is inserted in the disc space. The plug P is then rotated 90° about the longitudinal axis X' as shown in FIGS. 14a, 14c and 14d to distract the vertebrae bones anteriorly and restore the lordotic curve to the spine. This same procedure is performed on the other side of the spine. The reason for inserting the plug P is to stretch the ligaments of the spine, which makes it easier to deploy the spinal implant device 10 when it is placed in the disc space.

Figure 15:
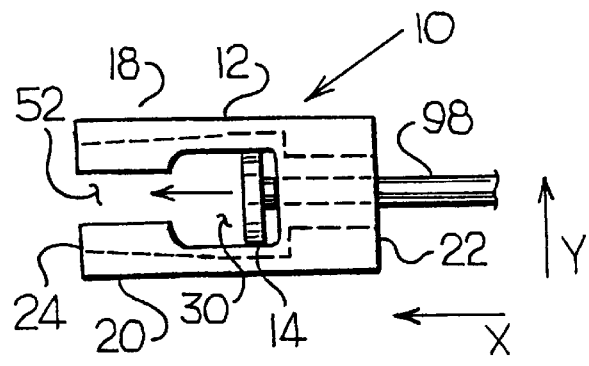
FIG. 15 is a side elevational view of the spinal implant device shown in FIG. 2 having a disc positioned therein from the forward end of the body.

Next, one of the plugs P is removed and the site is prepared by reaming out a hole (defined by the two adjacent vertebrae) having a diameter approximately equal to the width 26 of the first portion 16 for receipt of a spinal implant device 10. This reaming procedure will remove a small portion of the end plates of each vertebrae. The body 12, such as shown in FIGS. 2 and 3, is inserted into the hole. Preferably, the width W' of the second portion 18 is approximately equal to the width of the first portion 16. Initially, the second end 24 of the body 12 is forced into the implant receiving recess followed by the first end 22. At this point, the spinal implant device 10 has a substantially cylindrical profile, which means a cylindrical profile except for the flats 35. Alternatively, the profile can be completely cylindrical. Threaded inner surface 47 threadably receives a threaded end of a rod or plunger 98 as shown in FIG. 15. The direction of the threads defined on the threaded inner surface 47 is opposite from the direction of the threads defined on the outer surface 46. The plunger 98 is rotated about the longitudinal axis X threadably engaging with the threaded inner surface 47 of the disc 14. The disc 14 and the plunger 98 are moved in a first direction so that the disc 14 moves along the longitudinal axis X adjacent the surface 80. Then, the disc 14 is forced toward the second end 24 with the aid of the rod or plunger 98, which passes through the longitudinally extending passageway 44 that communicates with the disc receiving cavity 30 as shown in FIG. 15. This action forces and flexes the legs 18 and 20 in a lateral direction along the Y axis which, in turn, causes the adjacent vertebral bodies to move in the lateral direction, thereby causing a proper curvature of the spine. The disc 14 comes to rest adjacent to lips 68 and 70 as shown in FIG. 8 and in phantom in FIG. 6a. The plunger 98 is then rotated in a second direction about the longitudinal axis X and disengaged from the disc 14 and removed away from the passageway 44 resulting in an installed spinal implant device 10 as shown in FIG. 8.

Figure 16:
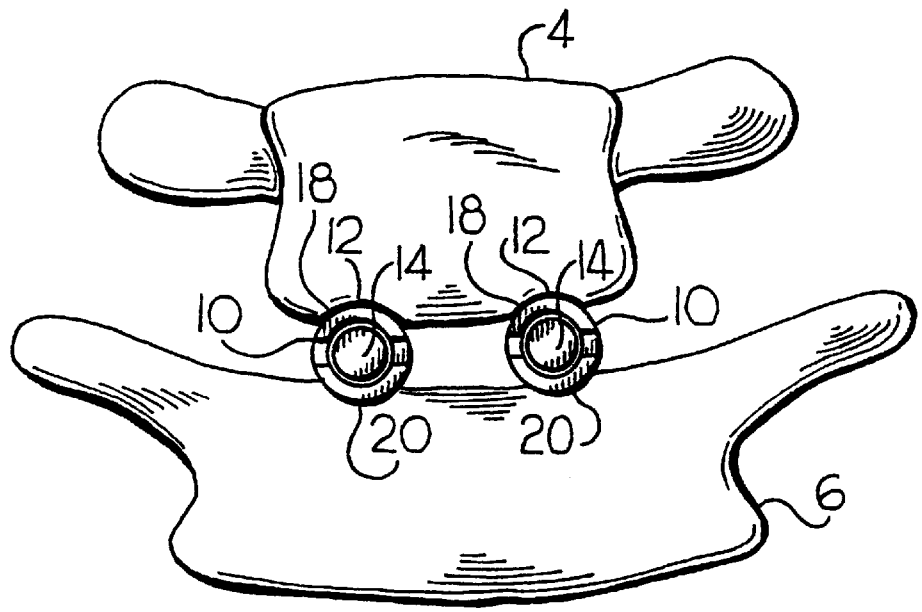
FIG. 16 is an end view of two spinal implants shown in FIG. 2 installed between two adjacent vertebrae.
Figure 17:
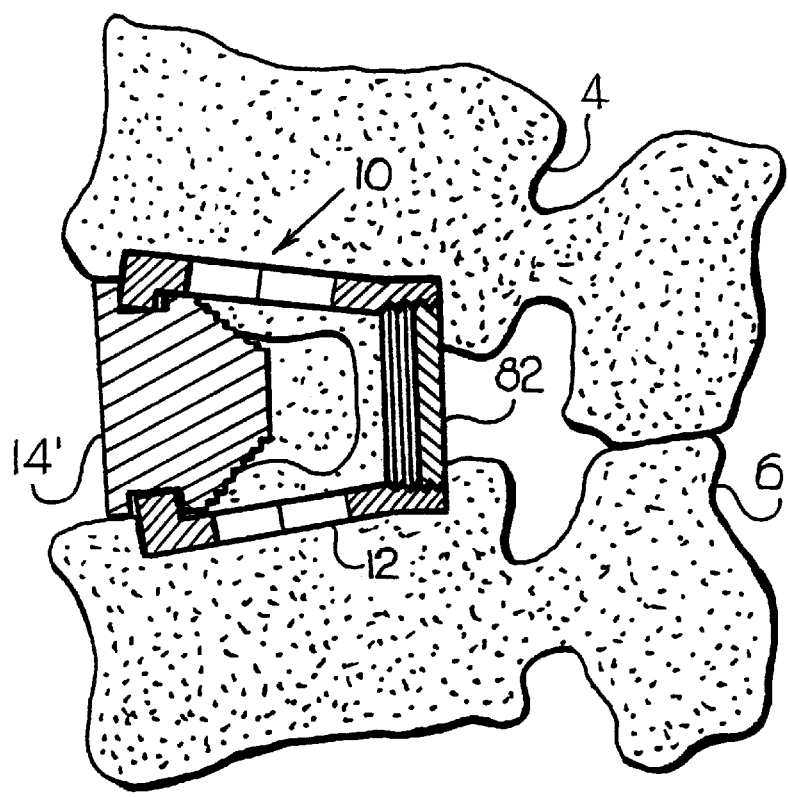
FIG. 17 is a partial, sectional view of the spinal implant device shown in FIG. 12 installed between two adjacent vertebrae.

The other plug P, which is now positioned adjacent to the installed spinal implant device 10, is removed and a second spinal device 10 is installed in a similar manner as described resulting in the spinal implant arrangement between two adjacent vertebrae 4 and 6 as shown in FIG. 16. The through-hole 51 and disc receiving cavity 30 define a bone receiving cavity 52. The bone receiving cavities 52 of both of the installed implant devices can then be packed with bone tissue. It is preferable to provide as much bone tissue in the bone receiving cavity 52. This can be accomplished by tamping the bone tissue in the bone receiving cavity 52. The passageways 36, 38 and 44 permit the harvested bone tissue to grow therethrough and fuse the adjacent vertebrae via arthrodesis. An optional plug 82 having a threaded end or snaps, which is preferably made from polyurethane or other non-metallic or metallic material, can be threaded or snapped into the first end 22. The threaded end of the plug 82 engages with the threaded inner surface 80 to plug through-hole 51 and prevent the bone mass from falling out of the body 12. Finally, the patient is sutured and the procedure is complete.

Installation of the spinal implant device 10 for anterior installation is described below. Initially, the disc area between two adjacent vertebrae is identified. The diseased spinal disc is removed. Plugs P are inserted and rotated to stretch the spinal ligaments as previously described. One plug P is then removed. A reamer reams out portions of adjacent vertebrae on one side of the spinal column forming a spinal implant receiving area. The threaded end plug 82 is first received by the threaded inner surface 80. The first end 22 of the body 12 is then placed in the spinal implant receiving area and the second end 24 is tapped by a mallet into the spinal implant receiving area until the body 12 is positioned between the two adjacent vertebrae. A second area is reamed between the two adjacent vertebrae on an opposite side of the spinal column forming a second spinal implant receiving area. The second body 12 is placed in the second spinal implant receiving area with the first end 22 preceding the second end 24. Bone tissue is placed within the bone receiving cavities 52 of both bodies. Then, discs 14' are engaged with lips 68 and 70 by rotating or screwing a respective disc 14' about the longitudinal axis X in a first direction until the circular portion 62 abuts against lips 68 and 70 and the surfaces 72 and 74 rest on circular portion 64 as shown in FIG. 12. Alternatively, disc 14' can be pushed toward the first end 22 of the body 12 until the circular portion 62 abuts the legs 68 and 70. Finally, the patient is sutured and the procedure is complete.

FIG. 18 shows another embodiment of a spinal implant device 90 made in accordance with the present invention. Specifically, the spinal implant device 90 includes a body 92 similar to the body 12, except an outer surface 94 of the body 92 is threaded. The threads extend from the first portion 16 to the legs 18 and 20 (not shown). All other aspects of the body 92 are the same as the body 12. The threaded body 92 provides radial projections to prevent the installed body 92 from dislodging. Radial projections or threads can be provided on the first portion 16 or either legs 18 and 20. The above-described installation procedure will further require threading the body 92 into the disc receiving areas as opposed to press fitting into place.

Figure 19:
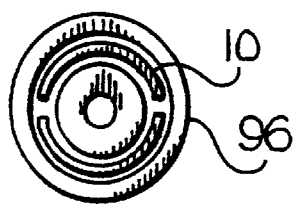
FIG. 19 is an end view of the spinal implant device shown in FIG. 2 received within a cannula.

With reference to FIG. 11, the body 12 can be provided with diverging legs 18 and 20. This arrangement can be inserted into the disc space through a cannula 96 as shown in FIG. 19 or clamps C can be provided. The clamps C are then removed prior to insertion of the disc 14 or 14' through the use of pliers, tweezers or the like.

Nitinol can be used for either body 12 or 92 whereby in one state the overall profile of the body is cylindrical as shown in FIG. 4 and after heat is applied from the human body, the legs 18 and 20 take on a tapered shape as shown in FIG. 11. The heat from the patient's body would be applied after the body 12 or 92 is received in the respective disc receiving area. Also, although only two legs 18 and 20 are shown, any number of legs can be provided to define the disc receiving cavity.

The present invention overcomes the deficiencies of the prior art cylindrical spinal implants and is easier to install than tapered implants. Further, the present invention provides a dynamic spinal implant through a one-piece body, which provides improved integrity over a multi-piece body and minimizes the number of mechanical components needed. Further, the present invention can be inserted posteriorly or anteriorly and can receive bone mass to facilitate healing.

Also, the present invention can be used at any location of the spine. Furthermore, since the present invention uses the same body 12 for anterior and posterior procedures, then the number of inventory parts required is minimized to one body 12, two discs 14 and 14' and an end cap 82 to perform either an anterior or posterior procedure. This will reduce the cost to manufacture the present invention.

Figure 20:
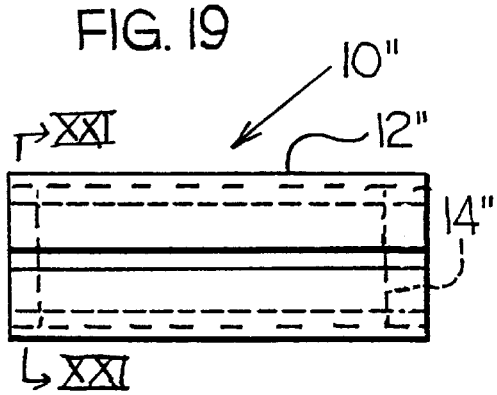
FIG. 20 is a rearward end view of another embodiment of a spinal implant device made in accordance with the present invention.
Figure 21:
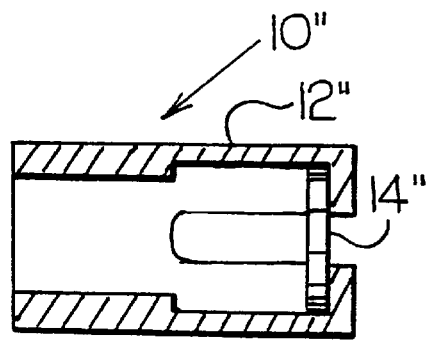
FIG. 21 is a sectional view taken along lines XXI—XXI of FIG. 20.

Finally, another embodiment of the present invention is a spinal implant device 10" that includes one rectangular shaped wide body 12" and a rectangular engaging member 14" that can be used in lieu of two bodies 12. The spinal implant device 10" is shown in FIGS. 20 and 21.

Having described the presently preferred embodiments of the invention, it is to be understood that it may otherwise be embodied within the scope of the appended claims.

I claim:

1. A dynamic fusion device for facilitating arthrodesis in a disc space between adjacent vertebrae, comprising:

a body extending along a longitudinal axis having a first portion and two or more legs depending from said first portion, said first portion having a first end having a width of a first lateral distance, said legs laterally spaced apart from each other and defining a second end of said body spaced opposite from said first end, said second end having a width of a second lateral distance, said legs defining an engaging member receiving cavity; and an engaging member secured to said body and received within said engaging member receiving cavity, wherein said engaging member is secured to said body only by engagement of said engaging member with said legs.

2. A dynamic fusion device for facilitating arthrodesis in a disc space between adjacent vertebrae as claimed in claim 1, wherein said engaging member slidably contacts said body whereby when said engaging member is positioned at a first position the second lateral distance approximately equals the first lateral distance and when the engaging member is positioned at a second position said engaging member causes said legs to flex and the second lateral distance is different than the first lateral distance.

3. A dynamic fusion device for facilitating arthrodesis in a disc space between adjacent vertebrae as claimed in claim 1, wherein when said engaging member is positioned at the second position the second lateral distance is greater than the first lateral distance.

4. A dynamic fusion device for facilitating arthrodesis in a disc space between adjacent vertebrae as claimed in claim 2, wherein said engaging member positioned at the second position is adjacent said second end.

5. A dynamic fusion device for facilitating arthrodesis in a disc space between adjacent vertebrae as claimed in claim 1, wherein said first portion is substantially cylindrical in shape.

6. A dynamic fusion device for facilitating arthrodesis in a disc space between adjacent vertebrae as claimed in claim 5, wherein said first portion is hollow.

7. A dynamic fusion device for facilitating arthrodesis in a disc space between adjacent vertebrae as claimed in claim 1, wherein said legs are spaced apart from each other defining a passageway through said body.

8. A dynamic fusion device for facilitating arthrodesis in a disc space between adjacent vertebrae as claimed in claim 7, wherein said legs define a passageway extending along an axis transverse to the longitudinal axis.

9. A dynamic fusion device for facilitating arthrodesis in a disc space between adjacent vertebrae as claimed in claim 1, wherein said first portion and said legs have curved outer surfaces, each of said outer surfaces having the same radius of curvature.

10. A dynamic fusion device for facilitating arthrodesis in a disc space between adjacent vertebrae as claimed in claim 1, wherein said body has an outer surface having a radial projection.

11. A dynamic fusion device for facilitating arthrodesis in a disc space between adjacent vertebrae as claimed in claim 10, wherein said body outer surface comprises a plurality of radial projections in the form of threads.

12. A dynamic fusion device for facilitating arthrodesis in a disc space between adjacent vertebra as claimed in claim 11, wherein said threads are defined on said first portion.

13. A dynamic fusion device for facilitating arthrodesis in a disc space between adjacent vertebrae as claimed in claim 1, wherein said first portion includes an inner surface that defines a hollow cavity that is in communication with the engaging member receiving cavity.

14. A dynamic fusion device for facilitating arthrodesis in a disc space between adjacent vertebrae as claimed in claim 1, further comprising an end cap, said first portion includes an inner surface defining a passageway having an open end, wherein said end cap attaches to said first end of said first portion and closes off the open end of the passageway.

15. A dynamic fusion device for facilitating arthrodesis in a disc space between adjacent vertebrae as claimed in claim 1, wherein said body is selected from the group consisting of titanium, nitinol and stainless steel.

16. A dynamic fusion device for facilitating arthrodesis in a disc space between adjacent vertebrae as claimed in claim 1, wherein said first portion is substantially cylindrical in shape and includes an inner surface that defines a hollow cavity that is in communication with the engaging member receiving cavity, said first leg and said second leg defining a passageway extending along an axis transverse to the longitudinal axis for bone mass to grow therethrough.

17. A dynamic fusion device for facilitating arthrodesis in a disc space between adjacent vertebrae as claimed in claim 16, wherein said body has an outer surface that includes a radial projection.

18. A method for installing a dynamic fusion device for facilitating arthrodesis in a disc space between adjacent vertebrae, said method comprising the steps of:

providing a body extending along a longitudinal axis having a first portion and two legs depending from said first portion, said first portion having a first end having a width of a first lateral distance, said legs laterally spaced apart from each other and defining a second end of said body spaced opposite from said first end, said second end having a width of a second lateral distance, said legs defining an engaging member receiving cavity; and an engaging member adapted to be secured to said body and received within said engaging member receiving cavity;

forming a body receiving passageway between two adjacent vertebrae for receipt of said body;

inserting said body into said body receiving passageway; and securing said engaging member to said second end of said body causing said legs to flex so that the second lateral distance increases whereby the second lateral distance is greater than the first lateral distance and the engaging member is only held in place by said legs.

19. A method as claimed claim 18, further comprising the step of placing bone tissue within the engaging member receiving cavity and a bone receiving cavity defined in said first portion of said body.

20. A method as claimed in claim 19, further comprising the step of securing an end cap to said first end of said body after bone tissue has been placed within said first portion.

21. A method as claimed in claim 18, further comprising the step of installing a second dynamic fusion device between the adjacent vertebrae which is adjacent to the installed fusion device.

22. A dynamic fusion device for facilitating arthrodesis in a disc space between adjacent vertebrae as claimed in claim 1, wherein said engaging member is secured to said second end of said body by moving said engaging member from a position external of said body to engage with said second end of said body.

23. A dynamic fusion device for facilitating arthrodesis in a disc space between adjacent vertebrae as claimed in claim 1, wherein at least one of said legs includes an inner surface that defines a ramp, whereby movement of said engaging member along the longitudinal axis contacts said ramp causing said leg to flex in a lateral direction and varying the second lateral distance.

24. A dynamic fusion device for facilitating arthrodesis in a disc space between adjacent vertebrae as claimed in claim 14, wherein said end cap is made of a polymeric material.

25. A dynamic fusion device for facilitating arthrodesis in a disc space between adjacent vertebrae as claimed in claim 1, wherein said first portion defines one or more passageways for permitting bone mass to grow therethrough.

26. A dynamic fusion device for facilitating arthrodesis in a disc space between adjacent vertebrae as claimed in claim 1, where said engaging member includes a threaded passageway for threadably receiving an adjustment rod for engaging said engaging member with said legs.

27. A dynamic fusion device for facilitating arthrodesis in a disc space between adjacent vertebrae as claimed in claim 1, wherein said engaging member is a disc.

28. A dynamic fusion device for facilitating arthrodesis in a disc space between adjacent vertebrae as claimed in claim 10, wherein said radial projection extends from at least one of said legs.

29. A dynamic fusion device for facilitating arthrodesis in a disc space between adjacent vertebrae as claimed in claim 11, wherein said threads are defined on said legs.

* * * * *

UNITED STATES PATENT AND TRADEMARK OFFICE
CERTIFICATE OF CORRECTION

PATENT NO. : 6,117,174
DATED : September 12, 2000
INVENTOR(S) : Wesley A. Nolan

It is certified that error appears in the above-identified patent and that said Letters Patent is hereby corrected as shown below:

Claim 18, Column 9, Lines 31-32 "cavity; " should read --cavity, --.

Signed and Sealed this

First Day of May, 2001

*Attest:*

NICHOLAS P. GODICI

*Attesting Officer*      *Acting Director of the United States Patent and Trademark Office*